United States Patent
Bayon et al.

(10) Patent No.: US 10,070,948 B2
(45) Date of Patent: Sep. 11, 2018

(54) BIOSYNTHETIC IMPLANT FOR SOFT TISSUE REPAIR

(71) Applicant: Sofradim Production, Trévoux (FR)

(72) Inventors: Yves Bayon, Lyons (FR); Philippe Gravagna, Charnoz (FR); Alfredo Meneghin, Laval (FR)

(73) Assignee: Sofradim Production, Trevoux (FR)

( * ) Notice: Subject to any disclaimer, the term of this patent is extended or adjusted under 35 U.S.C. 154(b) by 313 days.

(21) Appl. No.: 14/970,655

(22) Filed: Dec. 16, 2015

(65) Prior Publication Data

US 2016/0100926 A1 Apr. 14, 2016

Related U.S. Application Data

(62) Division of application No. 12/492,827, filed on Jun. 26, 2009, now Pat. No. 9,242,026.

(60) Provisional application No. 61/076,164, filed on Jun. 27, 2008, provisional application No. 61/076,166, filed on Jun. 27, 2008.

(51) Int. Cl.
| | |
|---|---|
| *A61F 2/00* | (2006.01) |
| *A61L 27/24* | (2006.01) |
| *A61L 27/26* | (2006.01) |
| *A61L 27/54* | (2006.01) |
| *A61L 27/56* | (2006.01) |
| *D04B 21/12* | (2006.01) |

(52) U.S. Cl.
CPC .......... *A61F 2/0063* (2013.01); *A61F 2/0077* (2013.01); *A61L 27/24* (2013.01); *A61L 27/26* (2013.01); *A61L 27/54* (2013.01); *A61L 27/56* (2013.01); *D04B 21/12* (2013.01); *A61F 2002/0068* (2013.01); *A61F 2002/0081* (2013.01); *A61L 2300/404* (2013.01); *A61L 2300/602* (2013.01); *D10B 2509/08* (2013.01)

(58) Field of Classification Search
CPC .................. A61F 2/0063; A61F 2/0077; A61F 2002/0068; A61F 2002/0081; A61L 27/24; A61L 27/56; A61L 2300/604; D10B 2509/08
USPC ...................................... 623/23.75
See application file for complete search history.

(56) References Cited

U.S. PATENT DOCUMENTS

| | | |
|---|---|---|
| 1,187,158 A | 6/1916 | Mcginley |
| 3,118,294 A | 1/1964 | Van Laethem |
| (Continued) | | |

FOREIGN PATENT DOCUMENTS

| | | |
|---|---|---|
| CA | 1317836 C | 5/1993 |
| DE | 19544162 C1 | 4/1997 |
| (Continued) | | |

OTHER PUBLICATIONS

Ellouali, M. et al., "Antitumor Activity of Low Molecular Weight Fucans Extracted from Brown Seaweed *Ascophyllu nodosum*," Anticancer Res., Nov.-Dec. 1993, pp. 2011-2020, 12 (6A).

(Continued)

*Primary Examiner* — Carson Gross

(57) ABSTRACT

An implant and a process for preparing such an implant are disclosed. The implant includes a porous layer including collagen, a non-porous layer including a collagenic constituent, and a reinforcement component. The non-porous layer is joined to the porous layer and the reinforcement member is embedded into the non-porous layer. The porous layer has a three dimensional density ranging from about 20 mg collagen/cm³ to about 200 mg collagen/cm³.

21 Claims, 5 Drawing Sheets

(56) References Cited

U.S. PATENT DOCUMENTS

| | | |
|---|---|---|
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,015,584 A | 5/1991 | Brysk |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,219,576 A * | 6/1993 | Chu ................ A61K 38/39 128/DIG. 8 |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Voumakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |

(56) References Cited

U.S. PATENT DOCUMENTS

| | | | |
|---|---|---|---|
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakamam et al. |
| 6,312,474 B1 | 11/2001 | Francis et al. |
| 6,328,686 B1 | 12/2001 | Kovac |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 * | 9/2002 | Ory .................. A61L 31/10 424/445 |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 * | 7/2003 | Melican ............ A61F 2/0045 424/426 |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,736,823 B2 | 5/2004 | Darois et al. |
| 6,743,435 B2 | 6/2004 | DeVore et al. |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,615,065 B2 | 11/2009 | Priewe et al. |
| 7,670,380 B2 | 3/2010 | Cauthen, III |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,931,695 B2 | 4/2011 | Ringeisen |
| 8,142,515 B2 | 3/2012 | Therin et al. |
| 8,197,837 B2 | 6/2012 | Jamiolkowski et al. |
| 8,323,675 B2 | 12/2012 | Greenawalt |
| 8,366,787 B2 | 2/2013 | Brown et al. |
| 8,709,094 B2 | 4/2014 | Stad et al. |
| 8,834,864 B2 | 9/2014 | Odar et al. |
| 8,846,060 B2 | 9/2014 | Archibald et al. |
| 8,877,233 B2 | 11/2014 | Obermiller et al. |
| 8,956,373 B2 | 2/2015 | Ford et al. |
| 9,034,357 B2 | 5/2015 | Stopek |
| 2002/0095218 A1 * | 7/2002 | Carr, Jr. ............ A61F 2/0063 623/23.72 |

(56) References Cited

U.S. PATENT DOCUMENTS

| | | |
|---|---|---|
| 2003/0086975 A1 | 5/2003 | Ringeisen |
| 2003/0114937 A1 | 6/2003 | Leatherbury et al. |
| 2003/0133967 A1* | 7/2003 | Ruszczak .............. A61L 15/325 424/443 |
| 2003/0225355 A1 | 12/2003 | Butler |
| 2004/0034373 A1 | 2/2004 | Schuldt-Hempe et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2007/0198040 A1 | 8/2007 | Buevich et al. |
| 2007/0299538 A1 | 12/2007 | Roeber |
| 2009/0035341 A1 | 2/2009 | Wagener et al. |

FOREIGN PATENT DOCUMENTS

| | | |
|---|---|---|
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1691606 A1 | 8/2006 |
| EP | 1782848 A2 | 5/2007 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 A1 | 3/2005 |
| FR | 2863277 A1 | 6/2005 |
| FR | 2876020 A1 | 4/2006 |
| FR | 2884706 A1 | 10/2006 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 02/007648 A1 | 1/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023444 A2 | 3/2006 |
| WO | 2007048099 A2 | 4/2007 |
| WO | 2009031035 A2 | 3/2009 |
| WO | 2009071998 A2 | 6/2009 |

OTHER PUBLICATIONS

Malette, W. G. et al., "Chitosan, A New Hemostatic," Ann Th. Surg., Jul. 1983, pp. 55-58, 36.

Langenbech, M. R. et al., "Comparison of biomaterials in the early postoperative period," Surg Endosc., May 2003, pp. 1105-1109, 17 (7).

(56) References Cited

OTHER PUBLICATIONS

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Surg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215, 126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 413-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Preliminary Search Report from French Patent Office dated Dec. 20, 2006, 3 pages.

\* cited by examiner

BIOSYNTHETIC IMPLANT FOR SOFT TISSUE REPAIR

CROSS-REFERENCE TO RELATED APPLICATIONS

This application is a divisional of U.S. patent application Ser. No. 12/492,827 filed Jun. 26, 2009, which claims benefit of and priority to U.S. Provisional Application No. 61/076,166 filed Jun. 27, 2008, and U.S. Provisional Application No. 61/076,164 filed Jun. 27, 2008, and the disclosures of each of the above-identified applications are hereby incorporated by reference in their entirety.

TECHNICAL FIELD

The present composite materials or implants have at least, a non-porous layer, a porous layer and a reinforcement member. The present composite materials or implants resist tearing when used in surgery, can simultaneously achieve hemostasis and prevent post-surgical adhesion wherever it is needed. They are particularly indicated for complex hernia, requiring resistance to microbial infection and a low speed of degradation during implantation. The present composite materials resist tearing when used in orthopedic surgery for tendon or ligament repair. They can support the repair/regeneration of soft tissues, under high stress/load.

DESCRIPTION OF THE RELATED ART

Implants for use in visceral surgery having a porous adhesive collagen layer closely associated with a collagen film are known. In this type of material, the film helps prevent the formation of post-operative adhesions and the porous adhesive collagen layer functions as a hemostatic compress.

Such implants are frequently secured to tissue during surgery using a surgical fastener, such as a staple, clip, tack, suture or the like. Collagen, however, weakens quickly when exposed to the moist conditions within the body during surgery. As a result, previous composite implants are prone to tearing during implantation.

In addition, the strength of such implants typically is too low for use under the high stresses or high loads encountered in orthopedic surgery, such as in tendon or ligament repair.

It would be advantageous to provide an implant having anti-adhesion, antimicrobial and relatively high strength properties and which resists tearing when subjected to the forces associated with securing the implant to tissue using surgical fasteners.

It would be advantageous to provide an implant having anti-adhesion, hemostatic and antimicrobial properties and which resists tearing when subjected to the forces associated with securing the implant to tissue using surgical fasteners.

In particular, it would be advantageous to provide an implant which maintains its properties, such as integrity, strength, resistance to tearing, porosity, thickness, when it is submitted to moist or wetted conditions, such as conditions encountered after implantation, when the implant is surrounded by biological fluids. It would also be advantageous to provide an implant which, although bioabsorbable in the long term (i.e., over one year), is long lasting, i.e., maintains its properties and integrity for at least 6 months.

SUMMARY

The present implants therefore aim to considerably improve the previously described composite collagenic materials with respect to their handling characteristics and resistance to tearing during implantation, their time of full degradation (over 1 year), their ability to withstand high loads and their resistance to microbial contamination during implantation, in particular when they are submitted to moist conditions such as implantation conditions, when they are surrounded by biological fluids. These aims are achieved by the present implants which include at least a non-porous layer, a porous layer and a reinforcement member. In embodiments, the non-porous layer is an oxidized collagen constituent-containing film possessing anti-adhesion properties. In embodiments, the porous layer is a collagen-containing foam that provides a matrix for soft tissue repair and/or regeneration, and that is long lasting and maintains its properties and integrity even in a wetted state. In embodiments, the reinforcement member is a mesh, such as a mesh having a weight density of below about 50 g/m$^2$. In other embodiments, the reinforcement member is a mesh, such as a mesh having a weight density of greater than about 100 g/m$^2$. The mesh, which can be knitted either from biodegradable yarns, non biodegradable yarns or any combination of thereof, may be fully coated with a collagen based formulation so as to limit the inflammation reaction and the infection risk associated with the yarns of the mesh. In other embodiments, the mesh is coated by any materials which can reduce the inflammation reaction and the infection risk.

Methods for producing the present implants are also described. In embodiments, the reinforcement member is fully coated with cross-linked collagens. Then a liquid solution based on oxidized collagen destined to form the non-porous layer is cast on a substrate. The coated reinforcement member is applied to the solution, in embodiments becoming completely embedded therein, for example, by pressing the reinforcement member into the solution or by the application of additional solution on top of the original volume of solution. Prior to complete gelling, a pre-formed porous layer, made from long lasting collagenic formulation is laid on the surface of the gelling solution. Upon drying, the various components adhere to form the present implant.

One aspect of the present disclosure is an implant comprising:
  a porous layer comprising at least a collagen,
  a non-porous layer comprising a collagenic constituent, the non-porous layer being joined to the porous layer, and
  a reinforcement member,
  wherein the reinforcement member is embedded into the non-porous layer, and the porous layer has a three dimensional density ranging from about 20 mg collagen/cm$^3$ to about 200 mg collagen/cm$^3$.

According to the present application, the three dimensional density in collagen of the porous layer is measured as follows: the amount of collagen used for the preparation of the porous layer is initially weighed in mg and recorded. The dimensions, i.e., length, width and thickness, of the porous layer in the final product, either in a dry or wetted state, are measured in cm. As meant in the present application, a wetted state corresponds to the soaking of the porous layer, or of the implant, during 24 hours in water at ambient temperature (i.e., 18-25° C.). The three dimensional density of the porous layer in mg collagen/cm$^3$ results from the ratio of the amount weighed in mg over the volume measured in cm$^3$.

The porous layer of the implant of the present disclosure has a three dimensional density ranging from about 20 mg collagen/cm$^3$ to about 200 mg collagen/cm$^3$, either in a dry or wetted state. As a consequence, the porous layer of the implant of the present disclosure has a three dimensional density ranging from about 20 mg collagen/cm$^3$ to about 200 mg collagen/cm$^3$, in a dry state. Also, the porous layer of the implant of the present disclosure has a three dimensional density ranging from about 20 mg collagen/cm$^3$ to about 200 mg collagen/cm$^3$ in a wetted state, i.e., after soaking in water at ambient temperature (18-25° C.) during 24 hours. The porous layer of the implant of the present disclosure is therefore dense in collagen, i.e., it comprises a high ratio of collagen. Such a density allows the porous layer to be long lasting although the porous layer will degrade in vivo in the long term, i.e., over one year for example. For example, the porous layer of the implant of the present disclosure will not be degraded before 6 months after the implantation. At the same time, the porous layer of the implant of the present disclosure shows a good homogeneity and favors the cellular growth. In particular, the porous layer of the implant of the present disclosure maintains its properties, such as integrity, porosity, resistance to tearing, strength, thickness, even in moist conditions, i.e., in a wetted state, similar to the conditions of implantation, when the porous layer and/or the implant is surrounded by the biological fluids. In particular, the porous layer of the implant of the present disclosure maintains substantially its thickness after implantation: for example there is no increase of 50% of the thickness or decrease of two thirds of the thickness of the porous layer after immersion of the porous layer in water, i.e., in moist conditions similar to the implantation moist conditions.

In an embodiment, the three dimensional density ranges from about 50 mg collagen/cm$^3$ to about 150 mg collagen/cm$^3$.

In embodiments, the collagen of the porous layer comprises at least oxidized collagen.

In embodiments, the collagen of the porous layer further comprises a collagen crosslinked with a compound selected from glutaraldehyde, hexamethylene diisocyanate (HMDI) and mixtures thereof. For example, the compound is glutaraldehyde. Alternatively, the compound is hexamethylene diisocyanate.

In embodiments, the porous layer further comprises a chitosan.

In embodiments, the collagenic constituent of the non-porous layer is oxidized collagen.

In embodiments, the reinforcement member is a mesh having a weight density less than 100 g/m$^2$, for example less than 50 g/m$^2$. In such embodiments, in particular, the mesh may be isoelastic. By "isoelastic" is meant according to the present application that the mesh shows substantially similar elastic properties in all directions. Such meshes are particularly suitable for implants of the present disclosure intended to be used as reinforcement implants for hernia repair for example.

In other embodiments, the reinforcement member is a mesh having a weight density greater than 50 g/m$^2$, for example greater than 100 g/m$^2$. In such embodiments, in particular, the mesh may be asymmetric. By "asymmetric" is meant in the present application that the mesh shows significantly different elastic properties in at least two different directions, for example in two perpendicular directions. Such meshes are particularly suitable for implants of the present disclosure intended to be used as reinforcement implants for tendon and/or ligament repair for example.

In embodiments, the mesh may be coated with a collagen crosslinked with a compound selected from glutaraldehyde, hexamethylene diisocyanate (HMDI) and mixtures thereof.

In other embodiments, the mesh may be coated with a mixture of oxidized collagen and chitosan.

In embodiments, the implant comprises an additional non-porous layer. The additional non-porous layer may have the same composition or a different composition from the non-porous layer above. The additional non-porous layer may comprise an additional reinforcement member embedded therein. The additional reinforcement member may be identical to or different from the reinforcement member above.

In embodiments, the porous layer is biodegradable. By biodegradable is meant herein that all the components forming the porous layer will be completely degraded in vivo after a certain amount of time. The porous layer of the implant of the present disclosure is long lasting and therefore will not be completely degraded in vivo before 6 months after implantation.

Another aspect of the present disclosure is a process for preparing an implant having a porous layer, a non-porous layer, and a reinforcement member comprising the steps of:
a) Preparing a composition comprising at least a collagen, using purified fibers of collagen as starting material,
b) Freeze drying the composition of a) to obtain a porous layer,
c) Compressing the porous layer obtained in b) so as to obtain a three dimensional density ranging from about 20 mg collagen/cm$^3$ to about 200 mg collagen/cm$^3$,
d) Pouring a solution of a collagenic constituent onto a support to obtain a non-porous layer,
e) Applying a reinforcement member on a top surface of the non-porous layer obtained in d), and
f) Applying the compressed porous layer obtained in c) on the top surface of the non-porous layer, during gelification of the non-porous layer.

The starting material used for obtaining the porous layer of the process of the present disclosure is purified fibers of collagen. Such purified fibers of collagen are obtained by conventional techniques such as described in FR-A-2 715 309. For example, the collagen is extracted from porcine dermis by solubilization at acidic pH or by digestion with pepsin, and purified by saline precipitations according to known techniques (see for example FR-A-2 715 309). Dry collagen fibers are then obtained by precipitation of an acid solution of such a collagen by adding NaCl, and then washing and drying of the precipitate obtained with aqueous solutions of acetone.

Using purified fibers of collagen for preparing the porous layer of the implant of the present disclosure allows determining exactly the content of collagen in the resulting porous layer of the final product.

In embodiments, the porous layer is compressed in step c) so as to obtain a three dimensional density ranging from about 50 mg collagen/cm$^3$ to about 150 mg collagen/cm$^3$.

In embodiments, the collagen of the porous layer comprises at least oxidized collagen.

In embodiments, the collagen of the porous layer further comprises a collagen crosslinked with a compound selected from glutaraldehyde, hexamethylene diisocyanate (HMDI) and mixtures thereof.

In embodiments, the collagen of the porous layer further comprises a chitosan.

In embodiments, the collagenic constituent of the non-porous layer is obtained from purified fibers of collagen used as starting material.

In embodiments, in step e), the reinforcement member is pressed into the solution of the non-porous layer, without causing significant disruption of the portion of the layer of solution in contact with the support, so as to embed the reinforcement member completely within the non-porous layer.

Alternatively, in step e), following application of the reinforcement member, additional solution of the collagenic constituent of step d) may be applied in an amount sufficient to cover the reinforcement member, so as to embed the reinforcement member completely within the non-porous layer.

In embodiments, in step c), the porous layer is compressed so as to reduce its thickness from about 1.2 times to 5 times. For example, the porous layer obtained in c) has a thickness ranging from about 0.1 cm to 1.5 cm.

Another aspect of the present disclosure is an implant obtainable by a process as described above.

DETAILED DESCRIPTION

Figure 1:
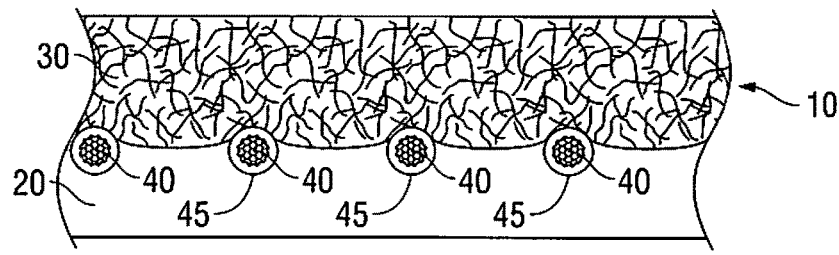
FIGS. 1-3 are schematic illustrations of composite materials in accordance with embodiments of the present disclosure.

The present implants include one or more non-porous layers, a porous layer and one or more reinforcement members. As seen in FIG. 1, composite implant 10 includes non-porous layer 20, porous layer 30 and reinforcement members 40, which in this illustrative embodiment are multifilament yarns coated with coating 45 and embedded within non-porous layer 20. Each of these components and processes for preparing each component and the composite implant are described in greater detail below.

Figure 2:
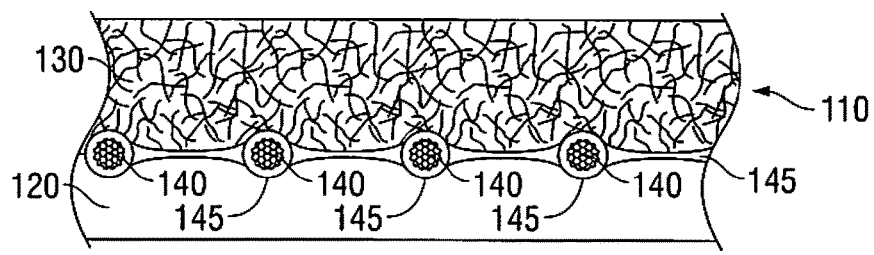
Figure 3:
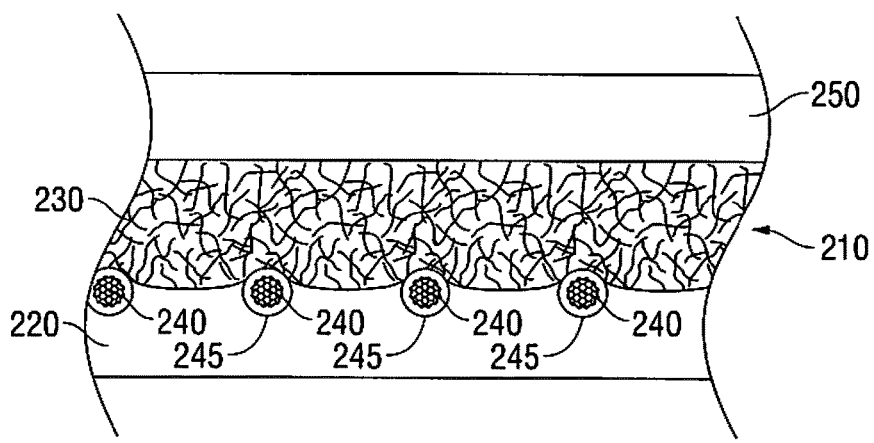

In the embodiment shown in FIG. 2, composite implant 110 includes non-porous layer 120, porous layer 130 and reinforcement members 140 which in this illustrative embodiment are multifilament yarns coated with coating 145 and embedded within non-porous layer 120. In the embodiment shown in FIG. 3, composite implant 210 includes non-porous layers 220 and 250, porous layer 230 and reinforcement member 240 with coating 245, which in this illustrative embodiment is embedded within non-porous layers 220.

Figure 5:
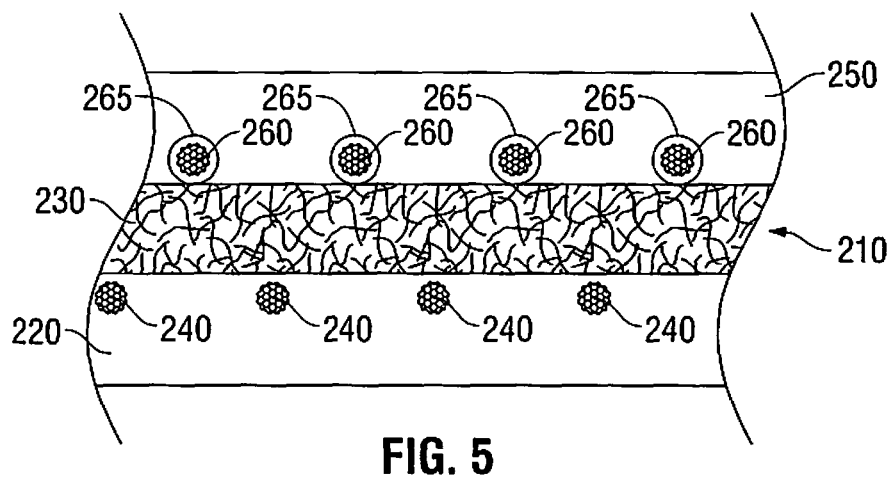
FIG. 5 is a schematic representation of a composite material in accordance with another embodiment of the present disclosure.
Figure 6:
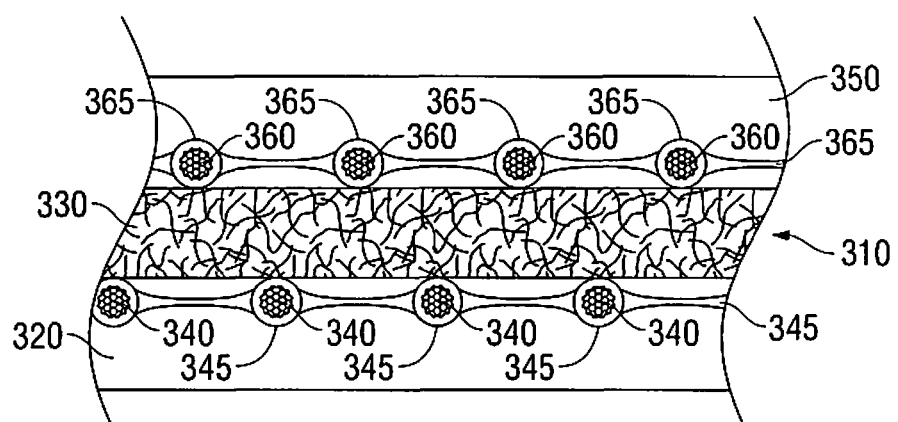
FIG. 6 is a schematic representation of a composite material in accordance with another embodiment of the present disclosure.

In the embodiment shown in FIG. 5, composite implant 210 includes non-porous layers 220 and 250, porous layer 230 and reinforcement members 240 and 260 coated with a coating 265, which in this illustrative embodiment are embedded within non-porous layers 220 and 250, respectively. In the embodiment shown in FIG. 6, composite implant 310 includes non-porous layers 320 and 350, porous layer 330 and reinforcement members 340 with coating 345, and 360 with coating 365, which in this illustrative embodiment are embedded within non-porous layers 320 and 350, respectively.

Each of these components and processes for preparing each component and the composite implant are described in greater detail below.

The Non-Porous Layer

The one or more non-porous layers may retard or prevent tissue ingrowth from surrounding tissues thereby acting as an adhesion barrier and preventing the formation of unwanted scar tissue. Thus, in embodiments, the one or more non-porous layers possesses anti-adhesion properties. By "non-porous layer" is meant according to the present application a layer having a surface substantially closed to all potential cellular growth, such as a film.

The one or more non-porous layers may be as well a physical barrier against microbial contamination.

The one or more (for example additional) non-porous layers of the present implant may be made from any biocompatible natural or synthetic material. The material from which each non-porous layer is formed may be the same or different and may be bioabsorbable or non-bioabsorbable. It should of course be understood that any combination of natural, synthetic, bioabsorbable and non-bioabsorbable materials may be used to form the one or more non-porous layers. Techniques for forming non-porous layers from such materials are within the purview of those skilled in the art and include, for example, casting, molding and the like.

Some non-limiting examples of materials from which a non-porous layer may be made include but are not limited to poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the one or more non-porous layers of the implant. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, and combinations thereof. In addition, the natural biological polymers may be combined with any of the other polymeric materials described herein to produce a non-porous layer of the implant.

In embodiments, the non-porous layer of the implant comprises at least a collagenic constituent.

In such embodiments, an aqueous solution of a collagenic constituent may be used to form a non-porous layer of the present implants. As used herein, the term "collagenic constituent" designates collagen which has at least partially lost its helical structure through heating or any other method, or gelatine. The term "gelatine" here includes commercial gelatine made of collagen which has been denatured by heating and in which the chains are at least partially hydrolyzed (molecular weight lower than 100 kDa). The collagenic constituent used may advantageously be formed of non-hydrolyzed collagen, mainly composed of α chains (molecular weight around 100 kDa). In the context of the present disclosure, α chains means complete α chains or fragments of these complete α chains produced by the loss of a small number of amino acids. The term "non-hydrolyzed" as used herein means that less than 10% of the collagenic chains have a molecular weight below about 100 kDa. If heating is used to denature the helical structure of the collagen, the heating should be moderate and provided under gentle conditions so as to avoid degradation by hydrolytic cleavage of the gelatine thus formed. Suitable gelatine materials are commercially available.

The collagen used can be of human or animal origin. It may particularly be type I porcine or bovine collagen, or type I or type III human collagen or mixtures in any proportions of the last two types. Native collagen may advantageously be used, in acid solution or after processing, to eliminate the telopeptides, notably by pepsin digestion. The collagen can also be oxidized: in such a case, the collagen may be modified by oxidative cleavage using any technique know to those skilled in the art, including, but not limited to the use of periodic acid or one of its salts as described by Tardy et al. in U.S. Pat. No. 4,931,546, the entire content of which is herein incorporated by reference. Briefly, this technique involves mixing the collagen in acid solution with a solution of periodic acid or one of its salts at a concentration of between about 1 and $10^{-5}$ M, in embodiments between about $5 \cdot 10^{-3}$ and $10^{-1}$ M, at a temperature of between about 10 and 25° C. for about 10 minutes to 72 hours. This process breaks down hydroxylysine and the sugars of the collagen, thus creating reactive sites without causing crosslinking. The oxidative cleavage of collagen allows moderate cross-linking later in the collagenic material. It should of course be understood that this function may be provided by other means of moderate cross-linking, for example by beta or gamma irradiation, or other agents of moderate cross-linking, for example chemical reagents at suitably low and non-toxic doses.

In embodiments, at least one of the non-porous layers of the present implant is made from collagen modified by oxidative cleavage as described above. In other embodiments, the extent of collagen cross-linking can be increased by any techniques known to those skilled in the art to adjust the degradation time of the non-porous layer as desired. As used herein, the term "moderately crosslinked" means that the degradation of the non-porous layer will be at least 90% complete (as measured by residual weight) by the end of about three weeks of implantation; the term "highly cross-linked" means that the degradation of the non-porous layer will be at least 90% complete (as measured by residual weight) by the end of about three months of implantation; and the term "extremely highly crosslinked" means that the degradation of the non-porous layer will be at least 90% complete (as measured by residual weight) by the end of about two years of implantation.

In embodiments, the collagen is advantageously formed of non-hydrolyzed collagen, mainly composed of a chains (molecular weight around 100 kDa). In the context of the present disclosure, a chains means complete a chains or fragments of these complete a chains produced by the loss of a small number of amino acids. The term "non-hydrolyzed" as used herein means that less than 10% of the collagenic chains have a molecular weight below about 100 kDa. If heating is used to denature the helical structure of the collagen, the heating should be moderate and provided under gentle conditions so as to avoid degradation by hydrolytic cleavage of the gelatine thus formed.

In embodiments, the collagenic constituent is oxidized collagen.

In such embodiments, a solution of oxidized collagen as defined above may be used to form the non-porous layer. Typically, a collagen concentration from about 5 g/l to about 50 g/l, in embodiments from about 25 g/l to about 35 g/l is used.

The solution of oxidized collagen may be heated, for example to a temperature in excess of 37° C., in embodiments to a temperature of from about 40° C. to about 50° C., for at least one hour. This results in at least partial denaturing of the collagen's helical structure. Other physical or chemical techniques for denaturing collagen (e.g., ultrasonication, or by the addition of chaotropic agents) are within the purview of those skilled in the art may also be used.

In embodiments, the collagenic constituent of the non-porous layer is obtained from purified fibers of collagen used as starting material. Such purified fibers of collagen are obtained as described below for the porous layer.

In embodiments, at least one macromolecular hydrophilic additive that is chemically unreactive with the collagenic constituent may be added to the solution used to form the non-porous layer. "Chemically unreactive with the collagenic constituent" as used herein means a hydrophilic compound which is not likely to react with the collagenic constituent, notably which does not form covalent bonds with it during cross-linking.

The macromolecular hydrophilic additive advantageously has a molecular weight in excess of 3,000 Daltons, in embodiments from about 3,000 to about 20,000 Daltons. Illustrative examples of suitable macromolecular hydrophilic additives include polyalkylene glycols (such as polyethylene glycol), polysaccharides (e.g., starch, dextran and/or cellulose), oxidized polysaccharides, and mucopolysaccharides. It should of course be understood that combinations of macromolecular hydrophilic additives may be used. In embodiments, polyethyleneglycol 4000 (4000 corresponding to the molecular weight) is added as the macromolecular hydrophilic additive. The concentration of hydrophilic additive(s) can typically be from about 2 to about 10 times less than that of the collagenic constituent. Typically, the macromolecular hydrophilic additive is eliminated by diffusion through the non-porous layer, in a few days.

Optionally, glycerine may be added to the solution used to form the non-porous layer. When present, the concentration of glycerine in the solution can typically be from about 2 to about 10 times less than that of the collagenic constituent, in embodiments less than about one-third of the collagenic constituent concentration.

In illustrative embodiments of the solution used to form the non-porous layer, the concentrations of collagenic constituent, hydrophilic additive(s) and glycerine, when present, can be from about 2% to about 10% for the collagenic constituent, from about 0.6% to about 4% for the hydrophilic additive(s) and from about 0.3% to about 2.5% for glycerine, respectively.

The solution used to form the non-porous layer may be prepared by adding collagenic constituent, hydrophilic additive(s) and glycerine, when present, to water or a water/alcohol (e.g., ethanol) mixture at a temperature of from about 30° C. to about 50° C. The solution may advantageously be neutralized to a neutral pH to avoid hydrolyzing the collagenic constituent by heating and to obtain a film of physiological pH while permitting pre-cross-linking of the collagenic constituent if the mixture contains oxidized collagen as indicated previously.

The Porous Layer

The porous layer of the implant has a three dimensional density in collagen which may prevent or reduce the risk of microbial contamination of the implant. By "porous layer"

is meant according to the present application a layer comprising pores, voids, holes allowing at least some cellular growth to take place.

The porous layer of the implant has for example openings or pores over at least a portion of a surface thereof. As described in more detail below, suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. Closed cell foams are illustrative examples of structures in which the pores may not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

The porous layer of the present implant may include any biocompatible natural or synthetic material. The material contained in the porous layer may be bioabsorbable or non-bioabsorbable. It should of course be understood that any combination of natural, synthetic, bioabsorbable and non-bioabsorbable materials may be used to form the porous layer. Some non-limiting examples of materials from which the porous layer may be made include but are not limited to poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and combinations thereof.

In embodiments, the porous layer comprises one or more bioabsorbable, natural biological polymer. Suitable natural biological polymers include, but are not limited to, collagen, gelatin, cellulose, hydroxypropyl cellulose, carboxyethyl cellulose, chitin, chitosan, and combinations thereof. Alternatively, the polymer constituent may be a polysaccharide such as chitin or chitosan, or polysaccharides modified by oxidation of alcohol functions into carboxylic functions such as oxidized cellulose. In addition, the natural biological polymers may be combined with any biocompatible synthetic materials to produce the porous layer of the implant.

Where the porous layer is a foam, the porous layer may be formed using any method suitable to forming a foam or sponge including, but not limited to the lyophilization or freeze-drying of a composition. Suitable techniques for making foams are within the purview of those skilled in the art.

The porous layer can be at least about 0.1 cm thick, in embodiments from about 0.2 to about 1.5 cm thick. The porous layer can have a two dimensional density of not more than about 100 mg collagen/cm$^2$ and, in embodiments, from about 10 mg collagen/cm$^2$ to about 50 mg collagen/cm$^2$. The two dimensional density of the porous layer is calculated by dividing the three dimensional density obtained as explained above by the thickness of the porous layer. The three dimensional density of the porous layer ranges from about 20 mg collagen/cm$^3$ to about 200 mg collagen/cm$^3$, in embodiments from about 50 mg collagen/cm$^3$ to about 150 mg collagen/cm$^3$, either in a dry state or a wetted state of the porous layer The size of the pores in the porous layer can be from about 10 μm to about 500 μm, in embodiments from about 20 μm to about 200 μm.

Such a porous layer, in particular having a three dimensional density ranging from about 20 mg collagen/cm$^3$ to about 200 mg collagen/cm$^3$, in embodiments from about 50 mg collagen/cm$^3$ to about 150 mg collagen/cm$^3$, either in a dry or wetted state, is long lasting, i.e., it is not degraded before 6 months after implantation. At the same time, the porous layer of the implant of the present disclosure shows a good distribution and interconnection of the pores, thereby allowing an excellent cellular growth.

The porous layer of the implant of the present disclosure comprises at least a collagen. By "collagen" is meant according to the present application, a non-denatured collagen or collagen which has at least partially lost its helical structure through heating or any other method.

The starting material used for obtaining the porous layer of the process of the present disclosure is purified fibers of collagen. Such purified fibers of collagen are obtained by conventional techniques such as described in FR-A-2 715 309. For example, the collagen is extracted from porcine dermis by solubilization at acidic pH or by digestion with pepsin, and purified by saline precipitations according to known techniques (see for example FR-A-2 715 309). Dry collagen fibers are then obtained by precipitation of an acid solution of such a collagen by adding NaCl, and then washing and drying of the precipitate obtained with aqueous solutions of acetone.

In embodiments, the porous layer is a made from non-denatured collagen or collagen which has at least partially lost its helical structure through heating or any other method, consisting mainly of non-hydrolyzed α chains, of molecular weight close to 100 kDa. The term "non-denatured collagen" means collagen which has not lost its helical structure. The collagen used for the porous layer of present implant may be native collagen or atelocollagen, notably as obtained through pepsin digestion and/or after moderate heating as defined previously. The origin and type of collagen may be as indicated for the non-porous layer described above.

In embodiments, the collagen of the porous layer comprises at least oxidized collagen. The oxidized collagen may be obtained as already described above for the non-porous layer.

In embodiments, the collagen may be cured to any desired degree. As used herein, the term "moderately cured" means that the degradation of the porous layer will be at least 90% complete (as measured by residual weight) by the end of about three weeks of implantation; the term "highly cured" means that the degradation of the porous layer will be at least 90% complete (as measured by residual weight) by the end of about three months of implantation; and the term "extremely highly cured" means that the degradation of the porous layer will be at least 90% complete (as measured by residual weight) by the end of about two years of implantation. In illustrative embodiments, moderately cured collagen is obtained by oxidative cleavage of collagen by periodic acid or one of its salts, as described for collagens of the non-porous layer. Highly cured collagen is made from collagen cross-linked by glutaraldehyde or by any other know cross-linking agents such as isocyanates, for example hexamethylene diisocyanate (HMDI). The degree of cross-linking distinguishes between highly cured and very highly cured materials. Techniques for curing to various degrees are within the purview of those skilled in the art.

In embodiments, the collagen of the porous layer further comprises a collagen crosslinked with a compound selected from glutaraldehyde, hexamethylene diisocyanate (HMDI) and mixtures thereof. For example, the compound is glutaraldehyde. Alternatively, the compound is hexamethylene diisocyanate.

In embodiments, the porous layer further comprises a chitosan.

The porous layer of the implant of the present disclosure may be obtained by freeze drying a composition comprising at least a collagen, using purified fibers of collagen as starting material.

In embodiments, the porous layer can be obtained by freeze-drying an aqueous acid solution or suspension of collagen at a concentration of about 2 to about 100 g/l and an initial temperature of about 4° C. to about 25° C. The concentration of collagen in the solution or suspension can be from about 10 g/l to about 100 g/l, in embodiments about 20 g/l.

The collagen suspension or solution can be made from non-cured, moderately cured, highly cured or extremely highly cured collagens or combinations of thereof at any proportions. It may include as well non collagenic components, such as glycosaminoglycans, among them chitosan. The glycosaminoglycans display a degree of acetylation (DA) of from about 0.5% to about 50%. They have a molecular weight ranging from about 100 to about 1,000,000 g/ml. It displays also a low polydispersity index of from about 1.2 to about 1.8. They may be a mixture of chitosans and other glycosaminoglycans (eg. hyaluronic acid), which have free amino groups capable of cross-linking to the oxidized collagen. In embodiments, the collagen suspension or solution is the combination of oxidized collagen and chitosan which can form a cross-linked network. As a result, in embodiments, the porous layer of the implant comprises oxidized collagen and chitosan, for example forming a network.

The porous layer is advantageously neutralized before its freeze-drying as a solution or suspension or after its freeze-drying under a dry form, at a pH from about 6 to about 8. In embodiments, the porous layer after its freeze-drying may be further cross-linked by any known cross-linking agents (e.g., glutaraldehyde, isocyanates) and/or by any physical treatment (e.g., thermal processing, gamma- and beta-irradiation).

The porous layer may be compressed so as to obtain a three dimensional density ranging from about 20 mg collagen/cm$^3$ to about 200 mg collagen/cm$^3$, for example ranging from about 50 mg collagen/cm$^3$ to about 150 mg collagen/cm$^3$.

For example, the porous layer may be further packed down by any relevant techniques so as to get a thickness from about 0.1 cm to about 1.5 cm and a 3D (three dimensional) density of from about 50 mg collagen/cm$^3$ to about 150 mg collagen/cm$^3$. The porous layer may be compressed so as to reduce its thickness from about 1.2 times to 5 times.

In any case where the porous layer is packed down, it may be further stabilized by thermal treatment, in dry conditions, at a temperature up to about 100° C., for up to 2 days or by cross-linking with any known cross-linking agents. In other embodiments, it may be further stabilized by soaking the porous layer in a collagenic solution such as an oxidized collagen solution and by drying this solution. Agents in the collagen solution/suspension such as glycerin may be as well added, before the freeze-drying, to stabilize the thickness of the porous layer.

In embodiments, the porous layer is biodegradable. By biodegradable is meant herein that all the components forming the porous layer will be completely degraded in vivo after a certain amount of time. The porous layer of the implant of the present disclosure is long lasting and therefore will not be completely degraded in vivo before 6 months after implantation.

The Reinforcement Member

The present implant also includes one or more reinforcement members. The reinforcement member may be positioned entirely within the non-porous layer.

The reinforcement member can be a mesh prepared using any technique known to those skilled in the art, such as knitting, weaving, tatting, knipling or the like. Illustrative examples of suitable meshes include any of those that are presently commercially available for hernia repair. In embodiments where a mesh is used as the reinforcement member, the mesh will aid in affixing the composite to tissue without tearing of the porous or non-porous layers.

It is envisioned that the reinforcement member may be formed from any bioabsorbable, non-bioabsorbable, natural, and synthetic material previously described herein including derivatives, salts and combinations thereof. In particularly useful embodiments, the reinforcement member may be made from a non-bioabsorbable material to provide long term flexible tissue support. In embodiments, the reinforcement member is a surgical mesh made from polyester, polypropylene, poly(lactic acid) (PLA), poly(glycolic acid) (PGA), oxidized cellulose, polycaprolactone (PCL), polydiaxanone (PDO), trimethylene carbonate (TMC), polyvinyl alcohol (PVA), polyhydroxyalkanoates (PHAs), polyamides, polyethers, copolymers thereof and mixtures thereof. In addition polyethylene materials may also be incorporated into the implant described herein to add stiffness. Where monofilaments or multifilament braids are used as the reinforcement member, any commercially available suture material may advantageously be employed as the reinforcement member.

It is envisioned as well that the reinforcing member may be knitted from bioabsorbable yarns, non bioabsorbable yarns or both of them, in any combination.

In embodiments, the mesh is a flat mesh, essentially a two dimensional mesh, displaying a thickness lower than about 1 mm. The mesh may be isoelastic or asymmetric while displaying mechanical properties (stiffness, elasticity at physiological loads) close to the tissues to be repaired and/or regenerated.

Figure 4:
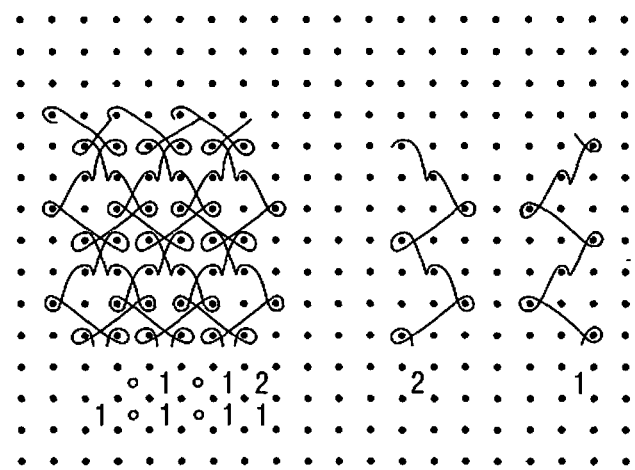
FIG. 4 shows a knitting pattern suitable for making a mesh reinforcement member for use in embodiments described herein.

In embodiments, the mesh weight density is below about 100 g per m$^2$, in embodiments, below about 50 g per m$^2$. The weight density of the mesh is determined according to the following method: the weight of the mesh is measured in grams; this weight is divided by the surface of the mesh in square meters. In such embodiments, the mesh may be isoelastic. Other characteristics which the reinforcement member may in embodiments advantageously possess include a breakage resistance of 100N minimum (as determined by ISO 13934-1) and an extension breakage of 20 to 40% under 50N (as determined by ISO 13934-1). Suitable fabrics suitable for obtaining isoelastic meshes can be made on a Rachel or warp knitting machine with at least two threading tools, one threaded full, one empty with PLA, PET or PP monofilament or multifilament biocompatible threads as shown in FIG. 4. When performed on a 22 or 24 gauge knitting machine, the macro-pores allow for a good integration to tissues. Such meshes are particularly suitable for implants of the present disclosure intended to repair an abdominal wall, for hernia treatment for example.

In other embodiments, the mesh is asymmetric, with a longitudinal axis displaying the highest mechanical properties and corresponding to the longitudinal axis of tendons and ligaments to be repaired.

In such embodiments, the ultimate load at break of the mesh in its longitudinal axis is from about 100N to about 1,000N, in embodiments over 250N (as determined by ISO 13934-1).

In such embodiments, the elongation at break of the mesh in its longitudinal axis is less than about 100%, in embodiments less than about 20% (as determined by ISO 13934-1). The elongation at 100 N is typically from about 1% to about 20%, in embodiments from about 1% to about 10% (as determined by ISO 13934-1).

The pores size of the mesh are from about 1 mm to 5 mm, in embodiments from about 1 mm to 2.5 mm.

In embodiments, in particular when the mesh is asymmetric, the mesh weight density is greater than about 50 g per $m^2$, in embodiments over 100 g per $m^2$.

In embodiments, the mesh is designed in such a way that it can be trimmed to the size of the defect to be repaired without any significant loss of the initial strain.

In embodiments, the mesh needs to hold sutures with a pull out strength of at least 100 N (as determined by ISO 13934-1).

In embodiments, the porosity of the mesh is from about 20% to about 98%, in embodiments from about 40% to about 95%. For the purpose of the present application, the porosity of a mesh is intended to mean a porosity measured in the following way: the dimensions, i.e., length, width and thickness, of the mesh, taken alone, are measured; moreover, the density of the yarns used to prepare the mesh is known. The mesh is weighed. By means of a simple subtraction, the volume occupied by the empty spaces within the mesh is deduced therefrom. The porosity over the entire mesh is determined as being the percentage of empty volume relative to the total volume of the mesh.

Figure 7:
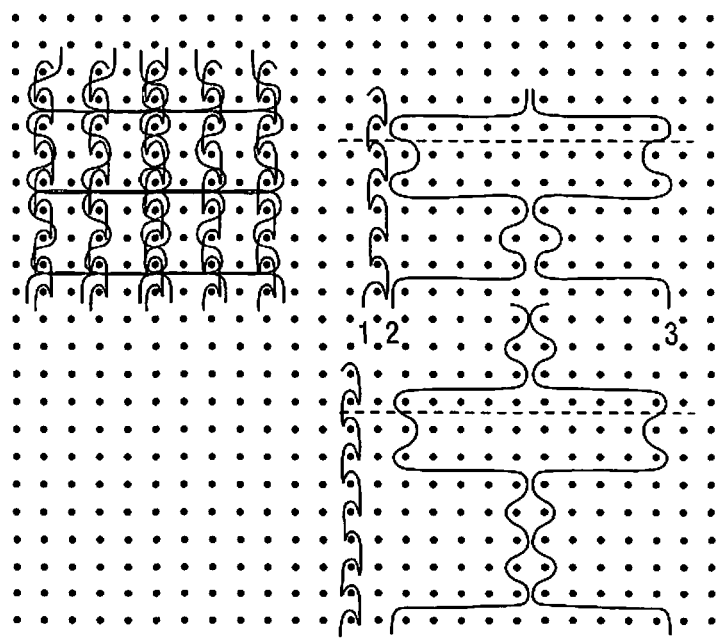
FIGS. 7-9 show illustrative knitting patterns suitable for use in making reinforcement components that may be incorporated into composite materials in accordance with embodiments of the present disclosure.

In embodiments, a suitable two dimensional fabric for obtaining an asymmetric mesh is prepared on a Rachel or warp knitting machine with three threading tool bars and a "marquisette" type weave, a bar forming a chain, two bars moving symmetrically as partial weft. (See FIG. 7) The number of crossings "under" a needle of these two weft bars determines the height of the opening. The three bars are one threaded full, one empty 22 or 24 gauge with standard thread or high tenacity thread count mini 150 dtex monofilament or mini 50 dtex multifilament.

Figure 8:
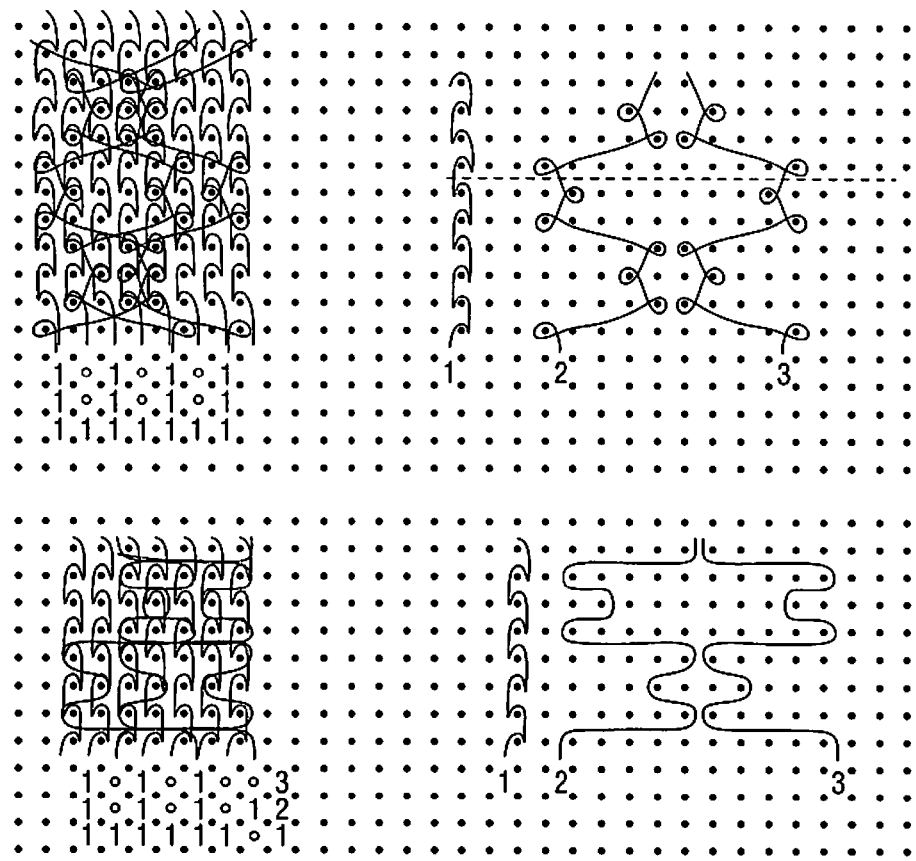

In other embodiments, another suitable two dimensional mesh is obtained with three knitting bars one of which is threaded full, with the two design bars one full and one empty. (See FIG. 8.)

Figure 9:
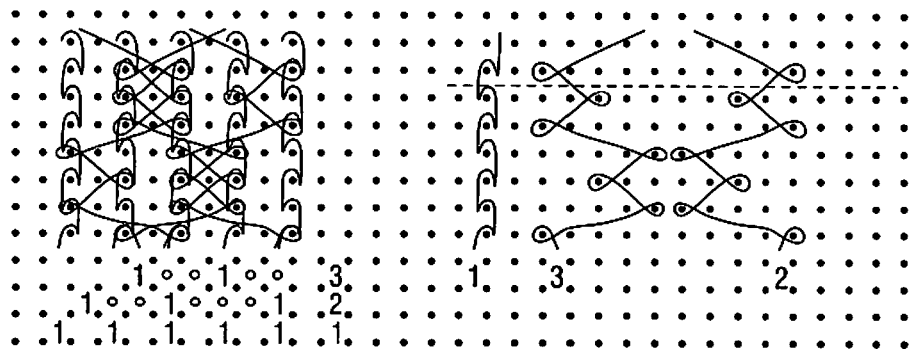

In yet other embodiments, another suitable two dimensional mesh is obtained with one full bar, one empty bar and two other one full and three empty (See FIG. 9.).

Coating of the Reinforcement Member

In embodiments, the reinforcement member is coated, so as to cover at least some of the surfaces of the reinforcement member. In embodiments, most of the accessible surfaces of the reinforcement member are covered. In some embodiments, the resulting coated reinforcement member may appear partially or fully embedded in the coating formulation. It is envisioned that the reinforcement member may be coated with any bioabsorbable, non-bioabsorbable, natural, and synthetic material previously described.

In the embodiment shown in FIG. 2, composite implant 110 includes non-porous layers 120, porous layer 130 and reinforcement members 140 which in this illustrative embodiment are multifilament yarns coated with coating 145 and embedded within non-porous layer 120. Where two reinforcement members are used, for example, a reinforcement member and an additional reinforcement member, each reinforcement member may be coated and the coating compositions may be the same or different on each reinforcement member. It is also envisioned that where two reinforcement members are used, one may be coated and one may remain uncoated. In the embodiment shown in FIG. 5, for example, only reinforcement member 260 includes a coating 265 while reinforcement member 240 is uncoated. In the embodiment shown in FIG. 6, composite implant 310 includes non-porous layers 320 and 350, porous layer 330 and reinforcement members 340 with coating 345 and 360 with coating 365, which in this illustrative embodiment are embedded within non-porous layers 320 and 350, respectively.

In embodiments where the reinforcement member is a mesh, it may be coated with a collagenic coating by soaking the mesh once, twice, three times or more in a collagenic solution or suspension. The collagen can be native collagen or gelatin, as described above. The collagen also may be chemically modified, by oxidation, esterification (e.g., methylation, ethylation, succinylation) or the like. At the end of each soaking cycle, the collagen layer laid on the mesh may be further cross-linked by any known cross-linking agents such as glutaraldehyde and isocyanates. Alternatively, the collagen is cross-linked once at the end of the overall soaking process.

Where the reinforcement member is a mesh, the soaking collagen solution or suspension may include non collagenic components, such as glycosaminoglycans, among them chitosan, as described above in connection with the porous layer. The coating may be made from oxidized collagen and chitosan. The layer of the collagenic solution or suspension may be neutralized with an alkaline bath at the end of each soaking cycle or only once when the overall soaking process is completed.

In embodiments, the mesh is coated with a collagen crosslinked with a compound selected from glutaraldehyde, hexamethylene diisocyanate (HMDI) and mixtures thereof. In other embodiments, the mesh is coated with a mixture of oxidized collagen and chitosan.

In some embodiments, where the reinforcing member is a mesh, the mesh may be pretreated by plasma or gas techniques for the formation of a layer containing bioactive agents such as antimicrobial agents (eg. DADMAC, Silver particles). For example, gas phase coating technology based on siloxane chemistry may be applied to the surface of the mesh where the siloxane thin film coating (<100 nm) material may include silver particles as described in the U.S. Pat. No. 6,984,392 and EP 1,691,606 B1.

Optional Bioactive Agents

In some embodiments, at least one bioactive agent may be combined with the implant and/or any of the individual components (the porous layer, the one or more non-porous layers, the one or more reinforcement members and/or the coating on the one or more reinforcement members) used to construct the implant. In these embodiments, the implant can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the medical device in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to poly(vinyl pyrrolidone), carboxymethyl cellulose, hyaluronic acid, polyethylene oxide, poly vinyl alcohols and combinations thereof.

Antimicrobial agents may be included as a bioactive agent in the bioactive coating and/or in the film layers of the present disclosure to reinforce the antimicrobial properties of the implant of the present disclosure. Suitable antimicrobial agents include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, biocide quaternary ammonium salts such as dimethyl diallyl ammonium chloride (DADMAC) and its derivatives, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives and oligomers of chitosan may be included as a bioactive agent in the bioactive coating of the present disclosure.

Other bioactive agents which may be included as a bioactive agent in the coating composition and/or in the film layer composition applied in accordance include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition and/or in the film layer composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Assembling the Implant

In an illustrative embodiment, the implant is prepared by first pouring a solution of collagenic constituent, destined to form a non-porous layer, such as a film, possibly containing the hydrophilic additive(s) and glycerine, onto an adequate, substantially flat support and distributing it evenly.

The support is inert in that it does not react with the above-mentioned components and is not involved in the cross-linking process. The support may advantageously be made from a hydrophobic material such as, for example, PVC or polystyrene. However, this support can also consist of a strippable material which will remain slightly adhesive and which can then be separated from the implant at the time of surgical use. This support may itself also consist of a film, for example dried collagen, onto which the solution is poured, or a layer of collagenic material gel in a distinctly more advanced state of gelification.

The density of the thin layer initially applied as a solution to the substrate can be from about 0.1 g solution/cm$^2$ to about 0.3 g solution/cm$^2$. This collagenic solution advantageously may be poured at a temperature from about 4° C. to about 30° C., and in embodiments from about 18° C. to about 25° C. Once applied to the substrate, the collagen solution is allowed to partially gel. Partial gelling results from cooling of the collagen solution, and not from drying of the solution.

A mesh reinforcement member is then applied to the solution. Application of the reinforcement member onto the solution means simply laying the reinforcement member onto the solution or partially gelled solution, and optionally applying slight pressing. The pressing should be insufficient to cause any significant disruption of the portion of the layer of solution in contact with the support/substrate thereby helping to maintain the integrity and anti-adhesion characteristics of the non-porous layer. The pressing may leave the surface of the reinforcement member exposed at the surface of the solution or may embed the reinforcement member completely within the layer of solution.

Following application of the mesh reinforcement member, but before complete gellification of the initially applied solution, additional solution may be applied in an amount sufficient to cover the mesh, so that it is completely embedded within the solution. Where pressing has already embedded the reinforcement member in the solution, application of additional solution may be eliminated.

This solution containing the embedded mesh reinforcement member is left to gel and a porous layer prepared as indicated above is applied to the solution during gelification.

Application of the porous layer onto the solution during gelification means simply laying the porous layer onto the gel, and optionally applying slight pressing. The pressing should be insufficient to cause any significant compaction of the porous layer. In embodiments where the porous layer has been pre-formed, the porous layer will become joined to the solution, but will not become interlocked with the mesh reinforcement member.

The moment at which the porous layer is applied to the solution during gelification will depend upon the nature of the solution employed, the conditions under which the solution is maintained during gelification and the nature of the porous layer. Generally, the solution will be allowed to gellify for a period of time prior to application of the porous layer such that the gel is still soft and allows the porous layer to penetrate over a distance which is advantageously from about 0.05 mm to about 2 mm and, in embodiments from about around 0.1 mm to about 0.5 mm. The appropriate moment for application of the porous layer for any given combination of materials/conditions can be determined empirically, for example by applying small samples of the porous layer to the gel at various times and evaluating the degree of penetration and adherence. Generally, when the solution which is gelling is at a temperature of between about 4 and 30° C., the porous layer can be applied from about 5 to about 30 minutes after the solution has been poured over the surface holding it.

The composite implant is left to dry or dried in order to obtain the final implant. When the collagenic solution destined to form the film includes oxidized collagen, it is polymerized while the material is drying. This drying occurs favorably at a temperature of from about 4° C. to about 30° C., in embodiments from about 18° C. to about 25° C. In other embodiments, the implant is further processed by adding a second non-porous layer on the other side, as described above. The material can be dried in a jet of sterile air if desired.

After drying, the implant can be separated from its support, packaged and sterilized using conventional techniques, e.g., irradiation with beta (electronic irradiation) or gamma (irradiation using radioactive cobalt) rays. In embodiments where hydrolytically unstable materials are used in forming the composite, such as polyglycolic acid, polylactic acid the composites are packaged under sufficiently dry conditions to ensure that no degradation of the composite takes place during storage.

The present implants are stable at ambient temperature and remains stable for long enough to be handled at temperatures which may rise to temperatures of from about 37 to 40° C. The thickness of the non-porous layer is not critical, but typically can be less than about 100 µm thick, and in embodiments from about 30 µm to about 75 µm thick. Likewise, the thickness of the porous layer is not critical, but typically can be from about 0.1 cm to about 1.5 cm thick, and in embodiments from about 0.3 cm to about 1.2 cm thick. The implants in accordance with this disclosure can be produced at a desired size or produced in large sheets and cut to sizes appropriate for the envisaged application.

The present composites may be implanted using open surgery or in a laparoscopic procedure. When implanted laparoscopically, the composite implant should be rolled with the porous side on the inside before trocar insertion.

The porous layer of the present implant can act as a long lasting support of the repair and/or regeneration of any soft tissues. The high density of the porous layer—from about 20 mg/cm$^3$ to about 200 mg/cm$^3$—protects the healing wound to some extent from bacteria and micro-organisms.

On the other hand, the implants described herein are particularly suitable for preventing post-operative adhesion, particularly in bleeding wounds, because the film prevents adherence. The non-porous layer also protects the healing wound for several days as it forms a barrier to bacteria and micro-organisms.

In embodiments where a mesh is used as a reinforcement member, the mesh will aid in affixing the composite to tissue without tearing of the porous or non-porous layers. The composite may be affixed to tissue using any conventional fastener, such as, for example, sutures, staples, tacks, two part fasteners, and the like. In embodiments, the fastener used to affix the composite to tissue is bioabsorbable, providing securement of the composite to a desired location long enough for tissue ingrowth to occur.

EXAMPLES

The following non-limiting examples show possible combinations of the materials and their hemostatic powers and ability to prevent post-operative tissue adhesions.

Example 1

1°) Obtention of Purified Fibers of Collagen

The collagen used is porcine collagen type I, extracted from porcine dermis by solubilization at acidic pH or by digestion with pepsin, and purified by saline precipitations according to known techniques (see for example FR-A-2 715 309). Dry collagen fibers obtained by precipitation of an acid solution of such a collagen by adding NaCl, and then washing and drying of the precipitate obtained with aqueous solutions of acetone having an increasing concentration of 80% to 100%, are used in the following steps of the present example.

2°) Preparation of Porous Layer a) Preparation of Glutaraldehyde-Crosslinked Collagen Purified fibers of collagen obtained in 1°) are solubilized in water at a final concentration of 1% in/v. The solution of collagen at 1% m/v is then neutralized by adding sodium phosphate at a final concentration of 20 mM. The final pH of the suspension was measured at between 6.5 and 7.5. Glutaraldehyde (aqueous solution of glutaraldehyde at 25%, m/v, sold by the company Fluka Chemie GmbH, Buchs, Switzerland) is then added to the suspension at a final concentration of 0.5% m/v. After two hours at ambient temperature, collagen fibers are recovered by filtration of the suspension through a nylon mesh. These fibers are then treated with sodium borohydride for at least two hours until the yellow coloration of the fibers has completely disappeared. The white fibers thus obtained are washed and neutralized at pH 6.5-7.5, and dried by removing the water with acetone. The acetone residues are then evaporated off.

b) Preparation of Oxidized Collagen

A 30 g/l solution of collagen is prepared by dissolving purified fibers of collagen obtained in 1°) in 0.01 N HCl. Its volume is 49 liters. Periodic acid is added to it at a final concentration of 8 mM, i.e., 1.83 g/l. Oxidation takes place at an ambient temperature close to 22° C. for 3 hours away from light.

Then an equal volume of a solution of sodium chloride is added to the solution to obtain a final concentration of 41 g/l NaCl.

After waiting for 30 minutes, the precipitate is collected by decantation through a fabric filter, with a porosity close to 100 microns, then washed 4 times with a 41 g/l solution of NaCl in 0.01 N HCl. This produces 19 kg of acid saline precipitate. This washing process eliminates all traces of periodic acid or iodine derivatives during oxidation of the collagen.

Then, several washes in an aqueous solution of 80% acetone are used to concentrate the collagen precipitate and eliminate the salts present.

A final wash in 100% acetone is used to prepare 3.6 kg of a very dense acetone precipitate of acid, oxidized, non-reticulated collagen, with no trace of undesirable chemical products.

The acetone paste is diluted with apyrogenic distilled water at ambient temperature, to obtain a 2% concentration of collagen.

c) Preparation of a Composition of Collagen Under the Form of a Collagenic Suspension A composition under the form of a suspension of collagen is prepared by mixing the glutaraldehyde-crosslinked collagen obtained in a) above and the oxidized collagen obtained in b) above, at the following concentrations:

0.5 to 3% m/v of glutaraldehyde-crosslinked collagen,
0.2 to 2% m/v of oxidized collagen.

d) Preparation of the Porous Layer by Freeze-Drying

The collagen suspension thus obtained in c) above is then lyophilized according to the following method: freezing is carried out as rapidly as possible, by decreasing the temperature of the product from 8° C. to −45° C., generally in less than 2 hours. Primary desiccation is initiated at −45° C., at a pressure of from 0.1 to 0.5 mbar. During this step, the temperature is gradually increased, with successive slopes and plateau, to +30° C. The lyophilization ends with secondary desiccation, at +30° C., for 1 to 24 hours. The vacuum at the end of secondary desiccation is between 0.005 and 0.2 mbar. The total lyophilization time is from 18 to 72 hours.

After the freeze-drying, the porous layer is packed down, in other words compressed, so as to reduce its thickness from about 1.2 times to about 5 times and so as to give the porous layer a three dimensional density ranging from 20 mg collagen/cm$^3$ to about 200 mg collagen/cm$^3$, either in the dry or wetted state.

The porous layer may be optionally treated with a solution of hexamethylene diisocyanate (HMDI) 0.1% w/v in acetone. The treatment period is about 20 hrs. The porous layer is then washed several times with acetone. The solvent is then eliminated by evaporation. HMDI may be replaced by any other suitable cross-linking agent such as glutaraldehyde, isocyanates (eg. isophorone diisocyanate), bifunctional or trifunctional glycidyl ethers, carbodiimides, acyl azides, divinylsulphone.

In any case, the porous layer is then heated at 50° C. for a period lasting between 15 and 24 hours to improve the cohesion and mechanical resistance of the lyophilized product during assembly of the composite.

3°) Preparation of a Solution of Oxidized Collagen Used to Form a Non-Porous Film Oxidized collagen is prepared as described above in 2°) b) in this example, but with minor modifications, at the end of the manufacturing process. The acetone paste is diluted with apyrogenic distilled water at 40° C., to obtain a 3% concentration of collagen, for a volume of 44 liters. The collagen suspension of a volume of 44 liters is heated for 30 minutes at 50° C., then filtered under sterile conditions through a membrane of 0.45 micron porosity in a drying oven at 40° C.

As soon as this solution is homogeneous and at 35° C., a sterile concentrated solution of PEG 4000 (polyethylene glycol with a molecular weight of 4000 Daltons) and glycerine is added to it to produce a final concentration of 0.9% PEG, 0.54% glycerine and 2.7% oxidized collagen.

As soon as these additions have been made, the pH of the solution is adjusted to 7.0 by adding a concentrated solution of sodium hydroxide.

4°) Coating of the Reinforcement Member

A knitted isoelastic, multifilament polylactic acid/polyester mesh reinforcement member is coated in a solution of type I porcine collagen at 0.8 m/v, by soaking it in the solution, with a padder, machine usually employed in the textile industry for coating process. This cycle of processes is repeated up to three times in order to obtain the full covering of the mesh.

At the end of the coating, the collagen deposited on the knit is cross-linked with glutaraldehyde at 0.5% m/v (aqueous solution of glutaraldehyde at 25%, m/v, sold by the company Fluka Chemie GmbH, Buchs, Switzerland), at neutral pH (pH between 6.5 and 7.5), for 2 hours, and is then reduced with sodium borohydride. The reagents used are removed by washing the knit with several water baths.

The cross-linking of the collagen deposited on the knit can alternatively be carried out at the end of each coating cycle.

5°) Preparation of a Biosynthetic Mesh for Soft Tissue Repair

An implant having a porous layer made from a composition that includes a collagen joined to a fiber-reinforced film made from a composition that includes a collagenic constituent is prepared. The collagen solution destined to form the non-porous layer, as described in 3°) above, is poured in a thin layer on a framed, flat hydrophobic support such as PVC or polystyrene, at an ambient temperature close to 22° C. The amount of solution used is 0.133 grams of solution per square centimeter of support. The collagen layer is let for about 15 min under a laminar flow hood. Then, the collagen coated reinforcement member obtained in 4°) above is pressed in the gelled collagen layer. The pre-made porous layer obtained in 2°) is then applied and adheres to the still sticky surface of the collagen solution.

The composite material is then dehydrated in a drying cabinet at 20° C. and 40% humidity with a horizontal flow of filtered air at a velocity of 1.2 m$^2$/s.

An implant is obtained, which is long lasting and resists tearing when put under moist conditions similar to conditions encountered during implantation. In particular, the implant of the present example maintains its integrity, its strength and its resistance to tearing even after being it soaked in water during 24 hours at ambient temperature (18-25° C.). Such an implant may be used for hernia repair.

Example 2

The product of Example 1 is further processed by adding a second non-porous layer on the other side. This second non-porous layer includes a second reinforcement member.

The collagen solution destined to form the second non-porous layer, as described in above Example 1, part 3°), is poured in a thin layer on a framed, flat hydrophobic support such as PVC or polystyrene, at an ambient temperature close to 22° C. The amount of solution used is 0.133 grams of solution per square centimeter of support. The collagen layer is let for about 15 min under a laminar flow hood. Then, a second collagen coated reinforcement member is pressed in the partially gelled collagen layer. Finally, the porous layer of the final product of Example 1 is laid on the partially gelled, second non-porous layer, in which the second reinforcement member is embedded.

The composite material is then dehydrated in a drying cabinet at 20° C. and 40% humidity with a horizontal flow of filtered air at a velocity of 1.2 m²/s.

An implant is obtained, which is long lasting and resists tearing when put under moist conditions similar to conditions encountered during implantation. In particular, the implant of the present example maintains its integrity, its strength and its resistance to tearing even after being it soaked in water during 24 hours at ambient temperature (18-25° C.). Such an implant may be used for hernia repair.

Example 3

1°) Preparation of Porous Layer

A composition of a collagen/chitosan mixture was prepared by mixing an acidic solution of oxidized collagen and an acidic solution of chitosan in different proportions with a final polymer concentration of 1% (w/w).

a) Oxidized Collagen

Oxidized collagen was obtained as described in the porous layer description of the Example 1, part 2°) b). A 2% w/v solution of oxidized collagen was obtained from the collagen paste, at ambient temperature.

b) Chitosan

The chitosan was solubilized in deionized water with a stoechiometric amount of hydrochloric acid with a polymer concentration of 3% (w/w). The pH of the chitosan solution was about 5, but the pH could have been adjusted to 3 to have better control of the crosslink kinetic between the oxidized collagen and chitosan.

c) Freeze Dried Composite

Several mixtures of various blends of oxidized collagen and chitosan as well as native collagen and chitosan (approximately 180 g) were obtained. Optionally, bioactive agents are included, such as antimicrobial agents. To the collagen preparation, may be added glycerol up to 1% w/v. The mixtures were poured within a 12 cm by 17 cm plastic box and freeze-dried for 48 hours. The samples were then neutralized in a 1M sodium hydroxide bath for 1 hour and thoroughly washed in deionized water until the pH reached 7. The freeze-dried sponges were then packed down, .i.e., compressed, to obtain a porous layer with a final thickness of 3 mm and a three dimensional density ranging from 20 mg collagen/cm³ to about 200 mg collagen/cm³, either in the dry or wetted state.

Additives, such as fucans, oligomers of chitosan, native or chemically modified glucosaminoglycans, which may induce self chemical crosslink between collagen and glucosaminoglycans (hyaluronic acid, sulphate chondroitin, etc), oxidized starch, and any other product which may enhance tissue repair, limit the risk of sepsis, and modulate the mechanical properties of the composite (swelling rate in water, tensile strength, etc) could have been added to the blend of oxidized collagen and chitosan.

The porous layer is then heated at a temperature equal or above 50° C. for a period lasting between 15 and 24 hours to improve the cohesion and mechanical resistance of the lyophilized product during assembly of the composite.

2°) Coating of the Reinforcement Member

A knitted isoelastic, multifilament polylactic acid/polyester mesh reinforcement member is soaked once, twice, or three times in an oxidized collagen/chitosan mixture with a padder, then dried and neutralized with an alkaline bath so as to cover the accessible surface of the mesh yarns. Alternatively, layers of oxidized collagen/chitosan mixture may be neutralized after each soaking cycles.

3°) Preparation of a Biosynthetic Mesh for Soft Tissue Repair

An implant having a porous layer made from a composition that includes a cross-linked network of oxidized collagen and chitosan joined to a fiber-reinforced film made from a composition that includes a collagenic constituent is prepared. The collagen solution destined to form the non-porous layer, as described in the Example 1, part 3°), is poured in a thin layer on a framed, flat hydrophobic support such as PVC or polystyrene, at an ambient temperature close to 22° C. The amount of solution used is 0.133 grams of solution per square centimeter of support. The collagen layer is let for about 15 min under a laminar flow hood. Then, the collagen coated reinforcement member as obtained in 2°) above is pressed in the gelled collagen layer. The pre-made, compressed porous layer as obtained in 1°) d) above is then applied and adheres to the still sticky collagen solution of the non-porous layer exposed through the pores of the mesh.

The composite material is then dehydrated in a drying cabinet at 20° C. and 40% humidity with a horizontal flow of filtered air at a velocity of 1.2 m²/s.

The composite material may be optionally treated with a solution of hexamethylene diisocyanate (HMDI) 0.1% w/v in isopropanol. The treatment period is about 20 hrs. The porous layer is then washed several times with acetone. The solvent is then eliminated by evaporation.

HMDI may be replaced by any other suitable cross-linking agent such as glutaraldehyde, other isocyanates, bifunctional or trifunctional glycidyl ethers, carbodiimides, acyl azides, divinylsulphone.

The porous layer can be further heated at about 50° C. for a period lasting between 15 and 24 hours to improve the cohesion and mechanical resistance of the lyophilized product during assembly of the composite An implant is obtained, which is long lasting and resists tearing when put under moist conditions similar to conditions encountered during implantation. In particular, the implant of the present example maintains its integrity, its strength and its resistance to tearing even after being it soaked in water during 24 hours at ambient temperature (18-25° C.). Such an implant may be used for hernia repair.

Example 4

1°) Collagen Used:

The collagen used are purified fibers of collagen as described in example 1, part 1°).

2°) Preparation of Porous Layer a) Preparation of a Composition of Hexamethylene Diisocyanate (HMDI)-Crosslinked Collagen Fifty grams of dry purified fibers of porcine collagen of 1°) above are mixed with 1 liter of acetone. One gram of HMDI is then added to the collagen suspension. The mixture is let, under agitation, overnight, at ambient temperature. Collagen fibres are then recovered by filtration of the suspension through a nylon mesh and are thoroughly washed with dry acetone to remove HMDI and acetone soluble HMDI byproducts. The cross-linked collagen fibres thus obtained are dried by removing the acetone residues. They may be further ground.

b) Preparation of Oxidized Collagen

Oxidized collagen is prepared from porcine collagen as described in Example 1, part 2°)b).

c) Preparation of the Collagenic Suspension

A composition under the form of a suspension of collagen is prepared by mixing the HMDI-crosslinked collagen of a) above, the oxidized collagen of b) above and, optionally glycerol, at the following concentrations:

0.5 to 3% w/v of HMDI-crosslinked collagen,
0.2 to 2% w/v of oxidized collagen,
0 to 1% w/v of glycerol d) Preparation of the Porous Layer by Freeze-Drying Several compositions as above in c) under the form of mixtures of various blends of oxidized collagen and HMDI-cross-linked collagen (approximately 180 g) were poured within a 12 cm by 17 cm plastic box and freeze-dried for 48 hours.

After the freeze-drying, the porous layer is packed down, i.e., compressed, so as to reduce its thickness from about 1.2 times to about 5 times and so as to obtain a three dimensional density ranging from 20 mg collagen/cm$^3$ to about 200 mg collagen/cm$^3$, either in the dry or wetted state.

The porous layer may be optionally treated with a solution of hexamethylene diisocyanate (HMDI) 0.2% w/v in acetone. The treatment period is about 20 hrs. The porous layer is then washed several times with acetone. The solvent is then eliminated by evaporation.

HMDI may be replaced by any other suitable cross-linking agent such as glutaraldehyde, isocyanates, bifunctional or trifunctional glycidyl ethers, carbodiimides, acyl azides, divinylsulphone.

In any case, the porous layer is then heated at a temperature above 50° C. for a period lasting between 15 and 24 hours to improve the cohesion and mechanical resistance of the lyophilized product during assembly of the composite.

3°) Coating of the Reinforcement Member

A knitted isoelastic, multifilament polylactic acid/polyester mesh reinforcement member is coated in a solution of type I porcine collagen at 0.8% m/v, by soaking it in the solution, with a padder, machine usually employed in the textile industry for coating process. This cycle of processes is repeated up to three times in order to obtain the full covering of the mesh.

At the end of the coating, the collagen deposited on the knit is cross-linked with HMDI. The knit is crosslinked in 100 ml of a phosphate buffer (0.054 M $Na_2HPO_4$, 0.013 M $NaH_2PO_4$, pH 7.4) containing 3% (w/w) HMDI and 1.0% (w/w) Tween 80 (polyoxyethylenesorbitan monooleate) as a surfactant for 20 h at room temperature. The knits are then rinsed for 30 min by running demineralized water, washed twice for 30 min with 4M NaCl and washed four times for 30 min with distilled water to remove unreacted HMDI or surfactant before drying the knit.

The cross-linking of the collagen deposited on the knit can alternatively be carried out at the end of each coating cycle.

4°) Preparation of a Biosynthetic Mesh for Soft Tissue Repair

An implant having a foam layer (porous layer) made from a composition that includes a collagen joined to a fiber-reinforced film made from a composition that includes a collagenic constituent is prepared. The collagen solution destined to form the non-porous layer, as described in the Example 1, part 3°) is poured in a thin layer on a framed, flat hydrophobic support such as PVC or polystyrene, at an ambient temperature close to 22° C. The amount of solution used is 0.133 grams of solution per square centimeter of support. The collagen layer is let for about 15 min under a laminar flow hood. Then, the collagen coated reinforcement member of 3°) above is pressed in the gelled collagen layer. The pre-made, compressed porous layer obtained in 2°) above is then applied and adheres to the still sticky collagen solution exposed through the pores of the mesh.

The composite material is then dehydrated in a drying cabinet at 20° C. and 40% humidity with a horizontal flow of filtered air at a velocity of 1.2 m$^2$/s.

A second non-porous layer may be further prepared by pouring the collagen solution as above in a thin layer on a framed, flat hydrophobic support such as PVC or polystyrene, at an ambient temperature close to 22° C. The amount of solution used is 0.133 grams of solution per square centimeter of support. The collagen layer is let for about 15 min under a laminar flow hood. Then, the porous layer of the composite material obtained above is pressed in the gelled collagen layer.

The resulting material is then dehydrated in a drying cabinet at 20° C. and 40% humidity with a horizontal flow of filtered air at a velocity of 1.2 m$^2$/s.

An implant is obtained, which is long lasting and resists tearing when put under moist conditions similar to conditions encountered during implantation. In particular, the implant of the present example maintains its integrity, its strength and its resistance to tearing even after being it soaked in water during 24 hours at ambient temperature (18-25° C.). Such an implant may be used for hernia repair.

Example 5

The product of Example 1 is further processed by adding a second non-porous layer on the other side.

The collagen solution destined to form the second non-porous layer, as described in Example 1, part 3°), is poured in a thin layer on a framed, flat hydrophobic support such as PVC or polystyrene, at an ambient temperature close to 22° C. The amount of solution used is 0.133 grams of solution per square centimeter of support. The collagen layer is let for about 15 min under a laminar flow hood. Then, the porous layer of the final product of Example 1 is laid on the partially gelled second non-porous layer.

The composite material is then dehydrated in a drying cabinet at 20° C. and 40% humidity with a horizontal flow of filtered air at a velocity of 1.2 m$^2$/s.

An implant is obtained, which is long lasting and resists tearing when put under moist conditions similar to conditions encountered during implantation. In particular, the implant of the present example maintains its integrity, its strength and its resistance to tearing even after being it soaked in water during 24 hours at ambient temperature (18-25° C.). Such an implant may be used for hernia repair.

Example 6

1°) Collagen Used:

The collagen used are purified fibers of collagen as described in example 1, part 1°).

2°) Preparation of the Porous Layer a) Preparation of a Composition of HMDI-Crosslinked Collagen Fifty grams of dry fibers of porcine collagen as obtained in 1°) above are mixed with 5 liters of demineralised water, under agitation. Once the solution is clear, the collagen is further neutralized and precipitated with 1N sodium hydroxide solution, at a pH ranging from 6.5 to 7.5. The collagen precipitate is collected by centrifugation (10 min, 10,000 rpm). The precipitate is washed by 3 successive acetone baths and is then completely dried. The yield of the neutralizing step of collagen is generally over 90%.

Forty grams of dry neutralized collagen is mixed with 0.8 liter of acetone. Two thousand and four hundred milligrams of HMDI is then added to the collagen suspension. The mixture is let, under agitation, from 6 to 20 hrs, at ambient temperature, under mild agitation. Collagen fibres are then recovered by filtration of the suspension through a nylon mesh and are thoroughly washed with dry acetone to remove HMDI and acetone soluble HMDI byproducts. This HMDI cross-linking step can be repeated once or twice. At the end, the cross-linked collagen fibres thus obtained are dried by removing the acetone residues. If needed, they may be further milled.

A test confirmed that the obtained HMDI cross-linked collagen is not substantially degraded by collagenase (Sigma), after 1 day in contact with collagenase, at +37° C. Generally, the degradation of the obtained HMDI cross-linked collagen by collagenase is less than 5% of its original amount whereas 65% or more of non cross-linked collagen is degraded in the very same conditions of the collagenase test.

b) Preparation of Oxidized Collagen

Oxidized collagen is prepared from purified fibers of porcine collagen as described in the Example 1, part 2°) b).

c) Preparation of a Composition Under the Form of a Collagenic Suspension

A suspension of collagen is prepared by mixing the HMDI-cross-linked collagen of a) above, and the oxidized collagen of b) above, at the following concentrations:
  0.7 to 3% w/v of HMDI cross-linked collagen,
  0.2 to 1.5% w/v of oxidized collagen.

d) Preparation of the Porous Layer by Freeze-Drying

Several compositions as above in c), under the form of mixtures of various blends of oxidized collagen and HMDI-cross-linked collagen (approximately 180 g) were poured within a 12 cm×17 cm plastic box and freeze-dried for 48 hrs.

After the freeze-drying, the porous layer is further packed down, ie compressed, with a press at a pressure between about 2 and about 12 bars, for a time ranging from 1 s to 20 s (Mader Pressen) and/or with an isostatic press (ACB, France), at a pressure between about 1,000 and about 1,500 bars, from about 1 minute to about 5 minutes, so as to reduce its thickness from about 1.5 to about 5 times, so as to get a final three dimensional collagen density ranging from about 50 mg/cm$^3$ to about 200 mg/cm$^3$, either in a dry or wetted state.

Ten grams of the porous layer is further neutralized in one liter of isopropanol/ethanol (95/5, v/v) containing from about 20 µmol to about 70 µmol of sodium hydroxide. The alcohol mixture is further removed by several washings with acetone. The porous layer is then treated with a solution of HMDI at a concentration of collagen of 50 grams per liter and at a concentration of HMDI ranging from about 0.1% to about 3% w/v. The mixture is let, under agitation, from 6 to 20 hrs, at ambient temperature, under mild agitation. The porous layer is then recovered by filtration removing acetone and is thoroughly washed with dry acetone to remove HMDI and acetone soluble HMDI byproducts. This HMDI cross-linking step can be repeated once or twice. At the end, the porous layer thus obtained is dried by removing the acetone residues.

A test has shown that the thus obtained porous layer is not substantially degraded by collagenase (Sigma), after 1 day in contact with collagenase, at +37° C. Generally, the degradation of the obtained HMDI cross-linked collagen by collagenase is less than 5% of its original amount whereas 65% or more of non cross-linked collagen is degraded in the very same conditions of the collagenase test.

3°) Coating of the Reinforcement Member

The coating reinforcement member is prepared as described in the Example 1, part 4°).

4°) Preparation of a Biosynthetic Mesh for Soft Tissue Repair

The biosynthetic mesh for soft tissue repair is prepared as described in Example 1, part 5°).

Example 7

1°) Preparation of a Biosynthetic Implant

A porous later has been prepared as described in the Example 6. The collagenic suspension is prepared by mixing the glutaraldehyde-cross-linked collagen and the oxidized collagen as obtained above in Example 6, at the following concentration:
  1.125% m/v of glutaraldehyde-cross-linked collagen,
  0.375% m/v of oxidized collagen.

Two hundreds and forty grams of this collagen suspension were poured within a 12 cm by 17 cm plastic box and freeze-dried for 48 hrs.

After the freeze-drying, the obtained porous layer was packed down, i.e., compressed, with the mechanical press (Mäger pressen) at 4 bars during two seconds and further packed down with the isostatic press (ACB, France) at 1,000 bars during 1 minute and then at 1,300 bars during 2 minutes.

The porous layer (50 grams) has been further treated with 1 liter of solution of HMDI at the concentration of 3% w/v in acetone, during 1 day. Then, the porous layer was extensively washed with acetone for removing HMDI and HMDI byproducts. The HMDI cross-linking step was repeated twice. At the end, the acetone was eliminated by evaporation.

The final thickness of the porous layer was about 1.5 mm with a corresponding three dimensional density of collagen at about 110 mg/cm$^3$, either in a dry or wetted state.

The obtained porous layer was then further assembled with a coated reinforcement member, the reinforcement member being an isoelastic polyester mesh available under the tradename Parietex® C, from the company Sofradim, and showing a weight density of about 110 g/m$^2$. The Parietex® C mesh was coated as described in Example 1, part 4°).

2°) Full Thickness Abdominal Wall Defect

Figure 10:
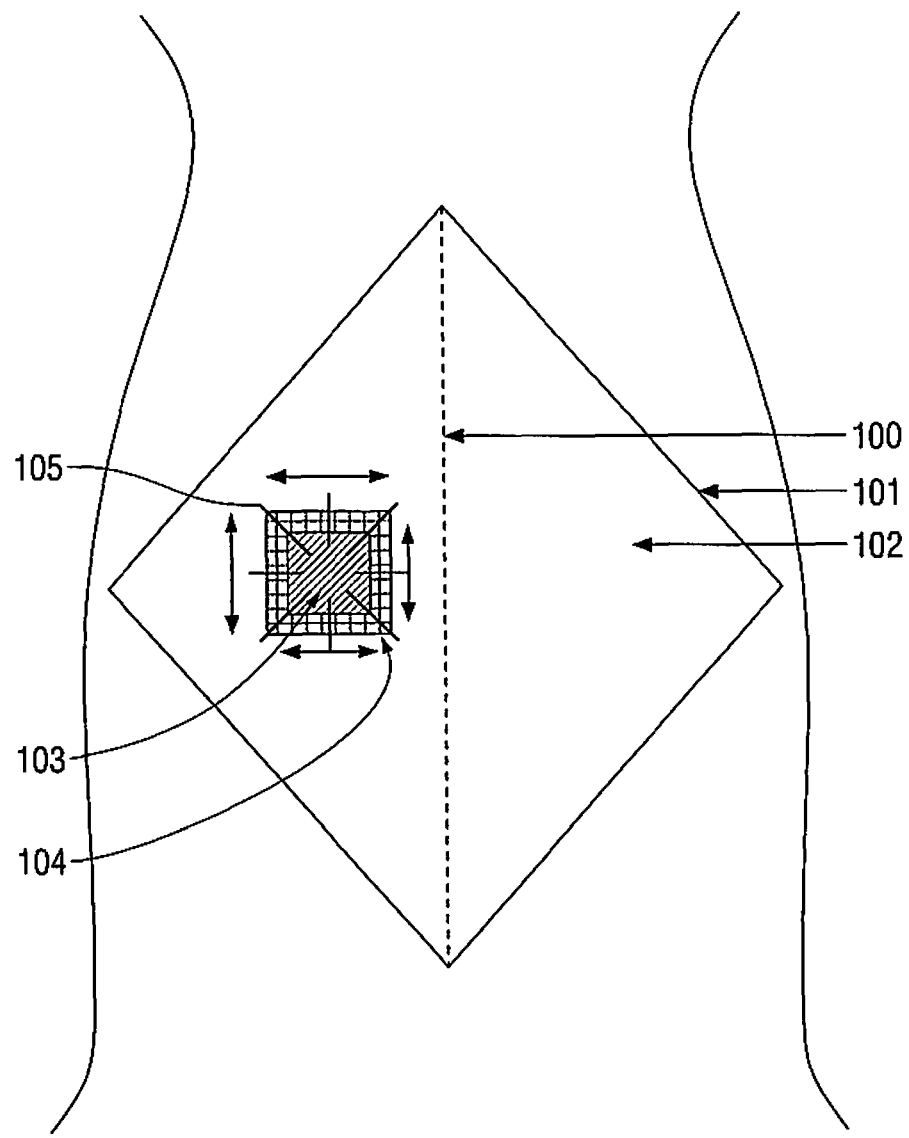
FIG. 10 is a schematic representation of an implanted implant in accordance with the present disclosure in a rat.

A full thickness abdominal wall defect model has been designed in rat for the evaluation of the biosynthetic implants of the present Example. The surgery consisted in creating a 1.5×3.0 cm full defect of the lateral anterior parietal wall (fascia, muscle and peritoneum). The defect was covered with a 2.0×3.5 cm implant. On FIG. 10 are shown schematically the llinea alba 100, the skin 101 and the abdominal muscles 102 of a rat.

As a prophylactic measure the rats received a pre-operative subcutaneous injections of carprofene (Pfizer) and enrofloxacine (Bayer). The abdomen was clipped free of fur. The skin was scrubbed and painted with povidone iodine (Vetoquinol). With reference to FIG. 10, a medial incision of the abdominal skin 101 was performed. The left external surface of the abdominal wall was exposed. A full thickness 1.5×3 cm square defect 103 was created within the abdominal musculature 102. The peritoneum was removed together with the abdominal muscular layer. One defect 103 was created per animal. Each defect 103 was covered with an approximately 2×3.5 cm square implant 104 obtained in 1°) above, as depicted on FIG. 10. One product/implant 104 was implanted per animal, with smooth side on the flank of the abdominal cavity. The product was sutured using absorbable sutures 105 (such as Monocryl 4-0, Ethicon, France). The skin 101 was closed by continuous intracutaneous absorbable sutures (Mersilk 1 4Ph., Ethicon, France). A dressing was applied on the abdomen.

Macroscopic and microscopic observations of the implants were made at 2 weeks and 4 weeks. They showed the nice integration of the implant, fully covering the defect, starting to be cell colonized in its full thickness. No obvious signs of herniation, in particular at the edges of the implant in the abdominal wall were noticed. No significant degradation of the implant, in particular the mesh itself and the porous layer, was as well observed, even after 4 weeks, It was noticed, even after 4 weeks of implantation, that the implant was not delaminated, for example having the mesh fully detached from the porous layer.

Example 8

The implant of EXAMPLE 7 was repeated, wherein the polyester Parietex® C mesh was replaced by an isoelastic polypropylene mesh available under the tradename Parietene® PPL from the company Sofradim and having a weight density of about 40 g/m².

Example 9

The implant of EXAMPLE 7 was repeated, wherein the polyester Parietex® C mesh was replaced by an isoelastic polyester mesh available under the tradename Parietex® CL from the company Sofradim and having a weight density of about 60 g/m².

Example 10

1°) Preparation of Porous Layers

The porous layers have been prepared as described in the Example 6. The collagenic suspension is prepared by mixing the glutaraldehyde-cross-linked collagen and the oxidized collagen obtained in Example 6 above, at the following concentrations:
Products A & B
  1.125% m/v of glutaraldehyde-cross-linked collagen,
  0.375% m/v of oxidized collagen.

A first product, the product A, was prepared by pouring one hundred and eighty grams of this collagen suspension within a 12 cm by 17 cm plastic box and freeze-dried for 48 hrs. After the freeze-drying, the obtained porous layer was packed down with the isostatic press (ACB, France) at 1,000 bars during 1 minute and then at 1,300 bars during 2 minutes. It has been packed in sealed aluminium I PET pouches, and further stored in an oven, at +103° C., during 1 day. It was then gamma-irradiated at a dose between 25 and 45 kGy and further heated at +50° C., during 2 days.

The final thickness of the porous layer was about 1.1 mm with a corresponding three dimensional density of collagen at about 135 mg/cm³, after its soaking in water during 24 hrs, at ambient temperature, i.e., in the wetted state of the porous layer.

A second product, the product B, was prepared by pouring two hundreds and forty grams of this collagen suspension within a 12 cm by 17 cm plastic box and freeze-dried for 48 hrs. After the freeze-drying, the obtained porous layer was packed down with the isostatic press (ACB, France) at 1,000 bars during 1 minute and then at 1,300 bars during 2 minutes. About 50 grams of the thus obtained porous layer has been further treated with 1 liter of solution of HMDI at the concentration of 3% w/v in acetone, during 1 day. Then, the porous layer was extensively washed with acetone for removing HMDI and HMDI byproducts. At the end, the acetone was eliminated by evaporation. It has been packed in sealed aluminium/PET pouches, and further stored in an oven, at +103° C., during 1 day. It was then gamma-irradiated at a dose between 25 and 45 kGy and further heated at +50° C., during 2 days.

The final thickness of the porous layer was about 0.9 mm with a corresponding three dimensional density of collagen at about 125 mg/cm³, after its soaking in water during 24 hrs, at ambient temperature, ie in a wetted state of the porous layer.

2°) Sub-Cutaneous Implantation of the Porous Layers A & B, in Rats

The sterile porous layers A & B, obtained as described above, were available as 10×20 mm pieces which were subcutaneously implanted in rats. The rats were sacrificed at 2, 4 and 12 weeks, after the implantation of the porous layers (three animals per time period with three sites per article and per time period). Macroscopic and histological observations have been performed for the evaluation of the implanted porous layers, in particular, for the evaluation of the local tolerance, the cellular or tissular colonization and implant degradation.

The study was based on the ISO10993 standard: Biological evaluation of medical devices, Part 6 (2007): Tests for local effects after implantation.

There was no evidence of morbidity or mortality during the study. No clinical abnormalities were detected during the course of the study. The porous layers A & B behaved in a similar way. At 2 weeks, the products were moderately integrated into the surrounding tissues with a moderate grade of cells and tissue colonization. A moderate grade of inflammation reaction was observed and products were slightly degraded by phagocytic cells. Very similar findings were observed at 4 weeks as compared to the 2 week time period with no fibrin and collagen deposit within the products, even if the product A showed better signs of colonization and integration. No significant increase of biodegradation was observed. At 12 weeks, very similar findings were also observed as compared to the previous time points (2 & 4 weeks), but with better tissue integration and cell colonization within the full thickness of the porous layers. The porous layers were slightly degraded with better resistance to degradation for the porous layer A.

At 2, 4 & 12 weeks, the initial thickness of the porous layers—as determined in a wet state, after the soaking of porous layers in water for 24 hours, at ambient temperature (18-25° C.), during 1 day—was not substantially reduced.

In conclusion, the local tolerance was good for the porous layers A & B with extended degradation times and with satisfying signs of cell colonization and integration of the porous layers.

It will be understood that various modifications may be made to the embodiments disclosed herein. Therefore, the above description should not be construed as limiting, but merely as an exemplification of illustrative embodiments. Those skilled in the art will envision other modifications within the scope and spirit of the present disclosure. Such modifications and variations are intended to come within the scope of the following claims.

What is claimed is:

1. A process for preparing an implant having a porous layer, a non-porous layer and a reinforcement member comprising:
preparing a composition comprising collagen, using purified fibers of collagen as starting material;
freeze drying the prepared composition to obtain a porous layer,
compressing the porous layer to obtain a three dimensional density ranging from about 20 mg collagen/cm3 to about 200 mg collagen/cm3;
pouring a solution of a collagenic constituent onto a support to obtain a non-porous layer;
applying a reinforcement member on a top surface of the non-porous layer, and
applying the compressed porous layer on the top surface of the non-porous layer, during gelification of the non-porous layer.

2. The process of claim 1, wherein the three dimensional density of the compressed porous layer ranges from about 50 mg collagen/cm3 to about 150 mg collagen/cm3.

3. The process of claim 1, wherein the collagen of the porous layer comprises oxidized collagen.

4. The process of claim 3, wherein the collagen of the porous layer further comprises a collagen crosslinked with a compound selected from glutaraldehyde, hexamethylene diisocyanate (HMDI) and mixtures thereof.

5. The process of claim 3, wherein the collagen of the porous layer further comprises a chitosan.

6. The process of claim 1, wherein the collagenic constituent of the non-porous layer is obtained from purified fibers of collagen used as starting material.

7. The process of claim 1, wherein applying the reinforcement member on the top surface of the non-porous layer further includes pressing the reinforcement member into the solution of the non-porous layer, without causing significant disruption of the portion of the layer of solution in contact with the support, so as to embed the reinforcement member completely within the non-porous layer.

8. The process of claim 1, further comprising applying additional solution of the collagenic constituent after applying the reinforcement member on the top surface of the non-porous layer, in an amount sufficient to cover the reinforcement member, so as to embed the reinforcement member completely within the non-porous layer.

9. The process according to of claim 1, wherein compressing the porous layer reduces the thickness of the porous layer by about 1.2 times to 5 times.

10. The process according to of claim 1, wherein the compressed porous layer has a thickness ranging from about 0.1 cm to 1.5 cm.

11. The process of claim 1, wherein the reinforcement member is a mesh having a weight density less than 100 g/m2.

12. The process of claim 11, wherein the mesh is isoelastic.

13. The process of claim 1, wherein the reinforcement member is a mesh having a weight density greater than 50 g/m2.

14. The process of claim 13, wherein the mesh is asymmetric.

15. The process of claim 13, further comprising coating the mesh with a collagenic coating.

16. The process of claim 15, wherein the collagenic coating comprises collagen crosslinked with a compound selected from glutaraldehyde, hexamethylene diisocyanate (HMDI) and mixtures thereof.

17. The process of claim 15, wherein the collagenic coating comprises a mixture of oxidized collagen and chitosan.

18. The process of claim 1, further comprising adding an additional non-porous layer.

19. The process of claim 18, wherein the additional non-porous layer comprises an additional reinforcement member embedded therein.

20. The process of claim 19, wherein the reinforcement member is coated and the additional reinforcement member is uncoated.

21. A process for preparing an implant having a porous layer, a non-porous layer and a reinforcement member comprising: freeze drying a composition comprising collagen to obtain a porous layer, compressing the porous layer to obtain a three dimensional density ranging from about 20 mg collagen/cm3 to about 200 mg collagen/cm3; pouring a solution of a collagenic constituent onto a support to obtain a non-porous layer; applying a reinforcement member on a top surface of the non-porous layer, and applying the compressed porous layer on the top surface of the non-porous layer, during gelification of the non-porous layer.

* * * * *